US008969781B2

(12) United States Patent
Hassibi et al.

(10) Patent No.: US 8,969,781 B2
(45) Date of Patent: Mar. 3, 2015

(54) INTEGRATED OPTICAL BIOSENSOR ARRAY INCLUDING CHARGE INJECTION CIRCUIT AND QUANTIZER CIRCUIT

(75) Inventors: Arjang Hassibi, Austin, TX (US); Rituraj Singh, Austin, TX (US); Arun Manickam, Austin, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 125 days.

(21) Appl. No.: 13/535,665

(22) Filed: Jun. 28, 2012

(65) Prior Publication Data

US 2014/0001341 A1    Jan. 2, 2014

(51) Int. Cl.
*H01J 40/14*    (2006.01)
*H01J 43/30*    (2006.01)

(52) U.S. Cl.
USPC ................................ 250/214 R; 250/214 LA

(58) Field of Classification Search
USPC .............. 250/214.1, 214 A, 214 LA, 214 LS, 250/214 AL, 226, 208.1; 330/67, 265, 271, 330/293, 310; 356/36–40, 239.7, 239.8, 356/244
See application file for complete search history.

(56) References Cited

U.S. PATENT DOCUMENTS

| 4,027,971 | A * | 6/1977 | Kolman et al. ................. 356/36 |
| 5,455,705 | A * | 10/1995 | Gusinov ........................ 398/202 |
| 6,330,092 | B1 * | 12/2001 | Aronson ....................... 398/152 |
| 7,995,679 | B2 * | 8/2011 | Ranganathan et al. ....... 375/340 |
| 8,023,113 | B2 | 9/2011 | El Gamal et al. |
| 2004/0080629 | A1 * | 4/2004 | Sato et al. .................. 348/222.1 |

OTHER PUBLICATIONS

Eltoukhy et al., "A 0.18-μm CMOS Bioluminescence Detection Lab-on-Chip," IEEE Journal of Solid-State Circuits, vol. 41, No. 3, pp. 651-662, Mar. 2006.
Rothberg et al., "The Development and Impact of 454 Sequencing," Nature Biotechnology, vol. 26, No. 10, pp. 1117-1124, Oct. 9, 2008.
Margulies et al., "Genome Sequencing in Microfabricated High-Density Picolitre Reactors," Nature, vol. 437, pp. 376-380, Sep. 15, 2005.

(Continued)

*Primary Examiner* — Georgia Y Epps
*Assistant Examiner* — Don Williams
(74) *Attorney, Agent, or Firm* — Winstead, P.C.

(57) ABSTRACT

An optical biosensor pixel for detecting the amount of light that is generated by the biosensing process and a biosensor array architecture that includes such biosensor pixels. The optical biosensor pixel includes a photodiode configured to convert an incident photon flux into a current. Additionally, the optical biosensor pixel includes an optical filter configured to select specific wavelengths and/or photon flux angles to reach the photodiode from a biological sample. The biosensor pixel further includes a trans-impedance amplifier coupled to the photodiode, where the trans-impedance amplifier is configured to convert the current into a voltage signal. Additionally, the biosensor pixel includes a 1-bit comparator coupled to the trans-impedance amplifier and a 1-bit digital-to-analog converter coupled to the 1-bit comparator, where the 1-bit digital-to-analog converter injects different levels of charge into an input of the trans-impedance amplifier at each cycle based on an output of the 1-bit comparator.

8 Claims, 12 Drawing Sheets

(56) References Cited

OTHER PUBLICATIONS

Schwartz et al., "A Single-Photon Avalanche Diode Array for Fluorescence Lifetime Imaging Microscopy," IEEE Journal of Solid-State Circuits, vol. 43, No. 11, pp. 2546-2557, Nov. 2008.

Singh et al., "A CMOS/Thin-Film Fluorescence Contact Imaging Microsystem for DNA Analysis," IEEE Transactions on Circuits and Systems, vol. 57, No. 5, pp. 1029-1038, May 21, 2010.

* cited by examiner

SEQUENCE LISTING

```
<160> NUMBER OF SEQ ID NOS: 1

<210> SEQ ID NO 1
<211> LENGTH: 12
<212> TYPE: DNA
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (1)..(12)

<400> SEQUENCE: 1
aaaccggttg cc                                                          12
```

INTEGRATED OPTICAL BIOSENSOR ARRAY INCLUDING CHARGE INJECTION CIRCUIT AND QUANTIZER CIRCUIT

TECHNICAL FIELD

The present invention relates generally to biosensors and bioelectronics, and more particularly to an optical biosensor array that includes pixels which consist of a photodetector and a dedicated embedded sensor circuitry that performs signal enhancement and/or signal processing.

BACKGROUND

Biosensors are devices that use biochemical reactions to identify and detect various molecules and biochemical analytes. Biosensors are widely used in different life-science applications, ranging from environmental monitoring and basic life science research to Point-of-Care (PoC) in-vitro diagnostics. Biosensors are known to be very sensitive and also extremely versatile in terms of detection and they can detect a small number of almost any kind of molecular structure, once a proper recognition molecule is identified. Example analytes that have been detected using biosensors include DNA and RNA strands, proteins, metabolites, toxins, micro-organisms, and even explosives molecules.

All biosensors, independent of the analyte they are trying to detect, include two key building blocks. One is the molecular recognition layer which is responsible for identifying and/or interacting with and/or reacting with and/or capturing the specific target analyte from the sample. The other is the sensor apparatus which detects and/or quantifies the interactions of the recognition layer with the analyte and provides a measurable output, generally in the form of an electrical signal. The molecular recognition layer typically comprises of carefully engineered and surface-assembled bio-molecules in the form of spotted or synthesized DNA oligonucleotides, aptamers, and antibodies attached to solid surfaces such as glass slides, micro-beads, electrodes, semiconductor materials, or dense polymers while the sensor includes optical-, MEMS- and/or electronics-based transducers connected to a low-noise circuit.

So far, there have been many detection methods that have been adopted in biosensor systems. A detection method is generally defined as the specific type of physiochemical mechanism designed into the molecular recognition layer, analytes, and the interaction environments that make the identification of the specific target analytes possible. The most widely used detection methods are different types of optical (e.g., fluorescence, bioluminescence) and electro-analytical (e.g., potentiometric, amperometric, impedimetric). It is also common to classify biosensors based on their detection method (e.g., in bioluminescence-based biosensors, the interaction of the analyte and probes results in a bioluminescence phenomenon which is detected by a specific sensor with a transducer sensitive to bioluminescence signals).

Currently, it has been difficult to build biosensors, such as optical biosensors, using Complementary Metal-Oxide Semiconductor (CMOS) processes thereby preventing the reduction of the bulkiness, complexity, etc. of the optical biosensors. Furthermore, there is not currently a biosensor array architecture that includes optical biosensors that overcome such limitations.

BRIEF SUMMARY

The principles of the present invention describe methods and architectures to address the challenges discussed in the Background and create high-performance optical biosensors in the CMOS processes.

In one embodiment of the present invention, an optical biosensor pixel comprises an integrated photodiode configured to convert an incident photon flux into a current. The optical biosensor pixel further comprises an integrated optical filter coupled to the integrated photodiode, where the integrated optical filter is configured to select specific wavelengths and/or photon flux angles to reach the integrated photodiode from a biological sample. Additionally, the optical biosensor pixel comprises a trans-impedance amplifier coupled to the integrated photodiode, where the trans-impedance amplifier is configured to convert the current into a voltage signal. Furthermore, the optical biosensor pixel comprises a quantizer circuit coupled to the trans-impedance amplifier, where the quantizer circuit is configured to convert a value of the voltage signal into a digital value. The optical biosensor pixel additionally comprises a charge injection circuit coupled to the quantizer circuit, where the charge injection circuit is configured to place a controllable current or a net charge into an input of the trans-impedance amplifier. In addition, the optical biosensor pixel comprises a feedback network coupled to the quantizer circuit, where the feedback network comprises the charge injection circuit, where the feedback network is configured to control an operation of the charge injection circuit based on values of the digital value.

In another embodiment of the present invention, an optical biosensor pixel comprises an integrated photodiode configured to convert an incident photon flux into a current. The optical biosensor pixel further comprises an optical filter coupled to the integrated photodiode, where the optical filter is configured to select specific wavelengths and/or photon flux angles to reach the integrated photodiode from a biological sample. Additionally, the optical biosensor pixel comprises a trans-impedance amplifier coupled to the integrated photodiode, where the trans-impedance amplifier is configured to convert the current into a voltage signal. The optical biosensor pixel further comprises a controlled voltage source coupled to a positive input of the trans-impedance amplifier. The optical biosensor pixel additionally comprises a 1-bit comparator coupled to the trans-impedance amplifier. In addition, the optical biosensor pixel comprises a 1-bit digital-to-analog converter coupled to the 1-bit comparator, where the 1-bit digital-to-analog converter injects different levels of charge into an input of the trans-impedance amplifier at each cycle based on an output of the 1-bit comparator.

In another embodiment of the present invention, a biosensor array architecture comprises a plurality of pixels assembled in rows and columns, where each of the plurality of pixels comprises an integrated photodiode configured to convert an incident photon flux into a current. Each of the plurality of pixels further comprises an optical filter coupled to the integrated photodiode, where the optical filter is configured to select specific wavelengths and/or photon flux angles to reach the integrated photodiode from a biological sample. Additionally, each of the plurality of pixels comprises a trans-impedance amplifier coupled to the integrated photodiode, where the trans-impedance amplifier is configured to convert the current into a voltage signal. Each of the plurality of pixels further comprises a controlled voltage source coupled to a positive input of the trans-impedance amplifier. Each of the plurality of pixels additionally comprises a 1-bit comparator coupled to the trans-impedance amplifier. In addition, each of the plurality of pixels comprises a 1-bit digital-to-analog converter coupled to the 1-bit comparator, where the 1-bit digital-to-analog converter injects different levels of charge into an input of the trans-impedance amplifier at each cycle based on an output of the 1-bit comparator. Additionally, the biosensor array architecture comprises row and column deciders coupled to the plurality of pixels, where the row and column deciders are configured to select individual pixels of the plurality of pixels.

The foregoing has outlined rather generally the features and technical advantages of one or more embodiments of the present invention in order that the detailed description of the present invention that follows may be better understood. Additional features and advantages of the present invention will be described hereinafter which may form the subject of the claims of the present invention.

BRIEF DESCRIPTION OF THE SEVERAL VIEWS OF THE DRAWINGS

A better understanding of the present invention can be obtained when the following detailed description is considered in conjunction with the following drawings, in which.

DETAILED DESCRIPTION

The principles of the preset invention relate to optical biosensors. Such biosensors detect the amount of light (i.e., photon flux) that is generated by the biosensing process and subsequently extract information regarding the analytes in the sample and the level of interactions that they have with the recognition layer. One typical example of an optical biosensor is the fluorescence-based DNA sensor, in which the intensity of light emitted from optical reporter molecules, such as fluorophore molecules, attached to the target DNA is used to track and detect the captured DNA. In these systems, the fluorescence emissions have to be triggered using an optical excitation source which operates at a different wavelength (usually shorter) compared to the emitted light. Such criterion requires a transducer and a sensor apparatus capable of detecting the generally small emission signal in the presence of the large excitation signal.

Methods to build "integrated optical biosensor arrays," which take advantage of Integrated Circuits (ICs) as their optical sensing apparatus are described herein. In these systems, the biosensor array is created by placing recognition layers in intimate proximity of a photodetector that is connected to an integrated sensor circuitry embedded in an IC. In the embodiments of the present invention, the photodetector array and the sensor circuitry in these systems are built using semiconductor micro-fabrication processes such as Complementary Metal-Oxide Semiconductor (CMOS).

It is noted that biosensor arrays, including the systems described herein, are essentially a plurality of densely packed biosensors that can detect multiple analytes in parallel from the sample. Individual sensors within the biosensor array are generally referred to as the "pixel" herein which in the context of the present invention consists of the photodetector and the dedicated embedded sensor circuitry that performs signal enhancement and/or conditioning, and/or digitization and/or signal processing.

Optical Pixel Architecture

Figure 1:
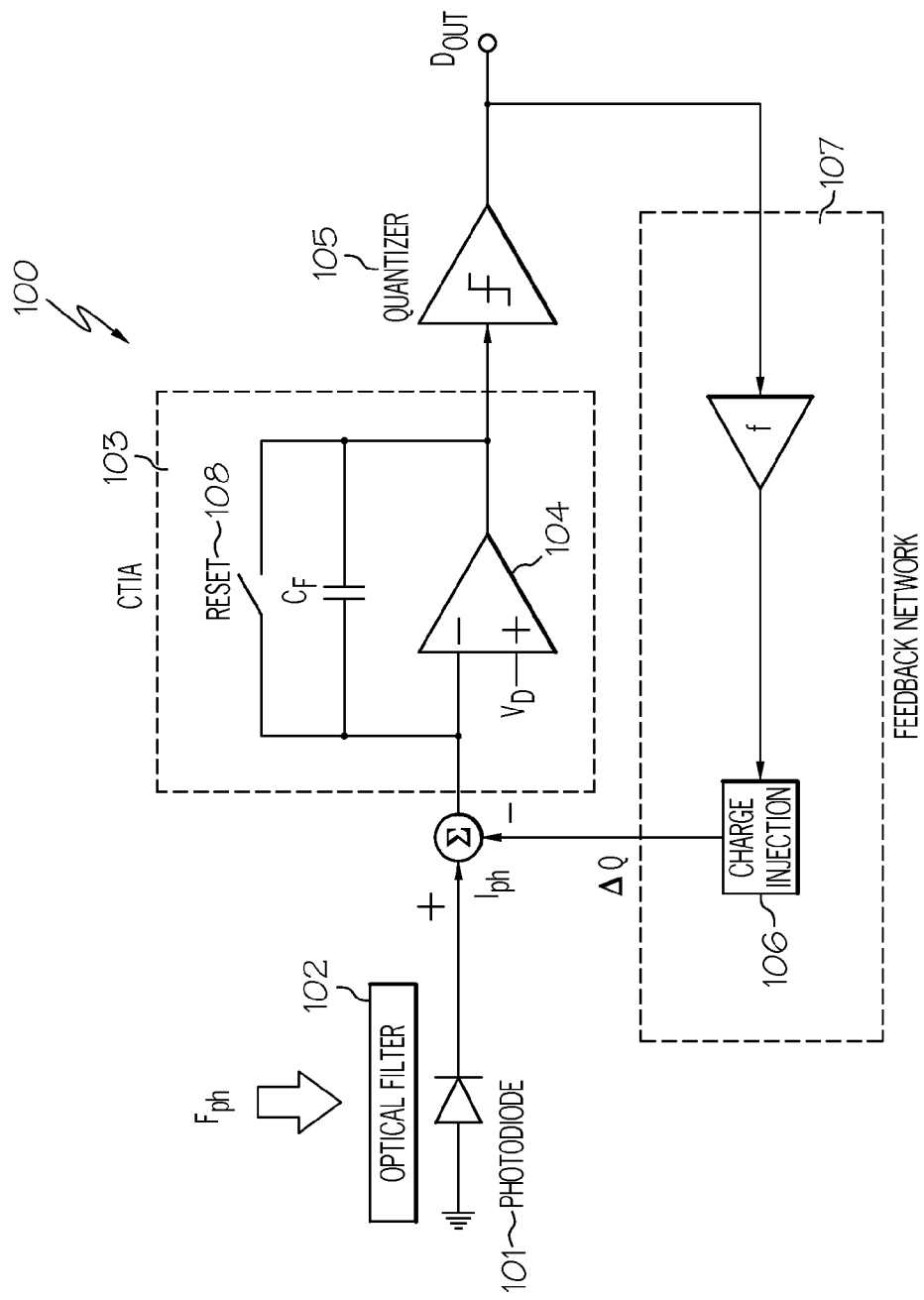
FIG. 1 illustrates the basic block diagram of a pixel in accordance with an embodiment of the present invention.

The integrated optical biosensor array, discussed herein, consists of a plurality of independent biosensing pixels (hence forth referred to as the pixel) densely packed in a 2-dimensional (2D) array. The number of pixels is typically greater than 10 and less than $10^8$. The basic block diagram of such a pixel 100 is shown in FIG. 1 in accordance with an embodiment of the present invention. In one embodiment, pixel 10 includes:

I. An integrated photodiode 101, which converts an incident photon flux into an electrical current, called the photocurrent $I_{ph}$.

II. An integrated optical filter 102 which selects only specific wavelengths and/or photon flux angles to reach integrated photodiode 101 from the biological sample.

III. A trans-impedance circuit (TIA) 103, which converts the $I_{ph}$ to a voltage signal. In the embodiments of the present invention, a capacitance trans-impedance amplifier (CTIA) is generally used, which converts an input current signal to a voltage by integrating the current onto its feedback capacitor, $C_F$, using an operational amplifier (op-amp) 104;

IV. A quantizer circuit 105, which converts the analog output voltage value of TIA (or CTIA) 103 into the digital value $D_{OUT}$;

V. A charge injection circuit 106, which can place a controllable current or net charge into the input of TIA (or CTIA) 103; and VI. A feedback network 107 which controls the operation of charge injection circuit 106 based on the values $D_{OUT}$.

The above blocks are described in detail in the following subsections:

Integrated Photodiode 101 (FIG. 1)

Figure 2:
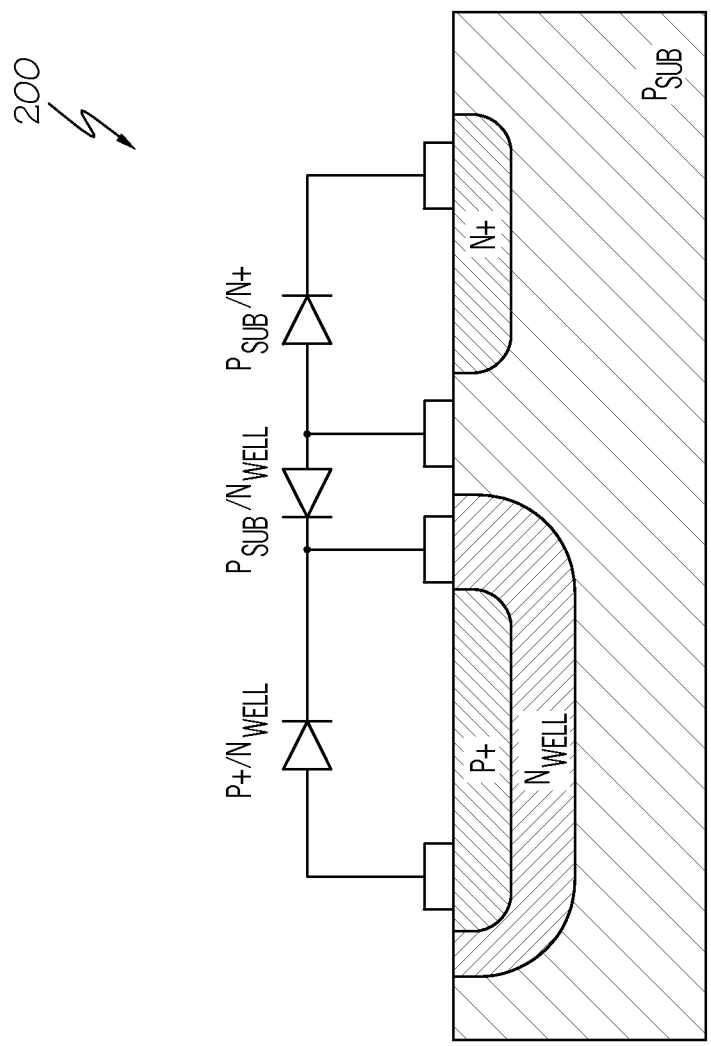
FIG. 2 illustrates possible photodiode devices in standard CMOS in accordance with an embodiment of the present invention.

Referring to FIG. 1, most ICs today are built using silicon micro-fabrication processes. The CMOS fabrication process is currently the "flagship" process within the semiconductor industry and the majority of ICs are built using this particular process. In a typical CMOS process, active devices (such as transistors) are fabricated in the silicon substrate; while interconnects (i.e., wirings) are built using aluminum (and occasionally copper) metal layers in thin layers on top of the silicon. While devices that are built in silicon (or CMOS) are optimized for electronic operation, there are a number of silicon-integrated devices that exhibit unique (and useful) optical behavior. It has been shown that the CMOS-integrated diodes, fabricated by doping the silicon substrates, have acceptable responsivity to light in the visible region of the electromagnetic spectrum and convert the incident photon flux, $F_{ph}$, into photocurrent, $I_{ph}$. It is widely known in the art that such devices, i.e., photodiodes 200, can be created by using the p+/nwell, nwell/psub, or n+/psub junctions available within any CMOS process as illustrated in FIG. 2 in accordance with an embodiment of the present invention, where each differ slightly in terms of responsivity and leakage (dark) current. Independent of what PN junction one uses, the photodiode should be biased in the reverse bias region to ensure that $I_{ph}$ is collected efficiently.

Integrated Optical Filter 102 (FIG. 1)

Referring to FIG. 1, it is important to realize that $F_{ph}$ may include additional signal components that are not related to the biosensing process in the pixel. Such signals can be categorized as interference or noise since they are generally non-informative or in some cases even disruptive. For example, if an optical biosensor array and densely packed pixels are created together, there is a possibility that a portion of light from analytes located at the nearby pixel can reach the photodiode (i.e., create a form of cross-talk) and contribute to the wrong $I_{ph}$. Another example is fluorescence detection and biosensors that use this particular optical detection modality, in which the relatively large and analyte-independent excitation signal can reach the embedded photodiodes and essentially overwhelm the analyte-dependent and informative part of $I_{ph}$ in each pixel.

One common approach to these impediments is to calibrate out such non-idealities after detection in software. However, in the present invention, optical filters 102 are relied upon to significantly mitigate this problem in hardware and at the pixel level. In the context of the present invention, optical filter 102 is defined as a micro-fabricated structure that is placed between the integrated photodiodes embedded in the IC and the sample where the photon flux is originating from. The function of optical filter 102 is to selectively pass the biosensing and analyte specific wavelength and/or incident angles of light and/or block the optical signal generated by other pixels. In other words, optical filter 102 can not only minimize the interference in terms of wavelength, but also can isolate pixels from one another to enable enhanced parallel detection.

There are different methods to implement optical filters. In some embodiments, filter 102 is created by placing a wavelength-selective planar layer on top of the IC. This layer can be made by depositing a plurality of dielectric materials periodically to form a thin-film multi-dielectric reflective filter. Example dielectric materials are $SiO_2$, $Si_3N_4$, and $TiO_2$ and the thickness range for each layer is typically between $\lambda/10$ to $\lambda$ for the passing light. The number of layers depending on the fidelity of the filter can vary between 2 to 100. In other embodiments, the layer is created by depositing a thin layer of materials with unique absorption spectra as an absorption optical filter. To minimize cross-talk, one can create angle-sensitive light-pipes which can only guide light from the correct biosensing location to the photodiode. An alternative approach is to physically create opaque barriers between pixels to block the passage of photons between pixels. In some embodiments of the present invention where the biosensor array is fabricated using a CMOS process, the optical filter, in the form of a metal curtain (see element 711 of FIG. 7B), can be used to isolate pixels and minimize cross talk. In such systems, the metal layers in process are used to create an opaque metal sheet around the periphery of the photodiode (i.e., the curtain) all the way from the silicon to the surface of the chip so that photon generated on top of the photodiode (where the associated analytes are for that pixel) can only hit the photodiode.

Capacitive Trans-Impedance Amplifier (CTIA) 103 (FIG. 1)

Referring to FIG. 1, CTIA 103 includes an opamp 104, a negative feedback capacitor $C_F$ (sometime referred to as the integrator capacitor), a reset switch 108 across $C_F$, and the voltage source $V_D$ which is connected to the positive terminal of opamp 104. In this system, if reset switch 108 is activated at t<0 and released at t=0, then the output of CTIA 103, denoted by $V_{OUT}$, at the end of the integration time $T_{int}$, becomes $$V_{OUT}(T_{int}) = \frac{1}{C_f} \int_0^{T_{int}} I_{pk}(t) dt + V_D \qquad (EQ\ 1)$$

which for a constant $I_{ph}$, can be simplified to $$V_{int}(T_{int}) = \frac{I_{pk} T_{int}}{C_f} + V_D \qquad (EQ\ 2)$$

One important characteristic of CTIA 103 is that the voltage at its input follows $V_D$. This is particularly useful when CTIA 103 is connected to photodiode 101 as it ensures that the voltage applied to its junction contact is set to $V_D$ and hence the voltage across the diode can be adjusted during the operation by simply changing $V_D$. As evident in (EQ 1) and (EQ 2), this has little effect on $V_{OUT}$ since changing $V_D$ only adds a known offset to its value.

Quantizer Circuit 105 (FIG. 1)

Referring to FIG. 1, quantizer circuit 105 compares $V_{OUT}(T_{int})$ to a single or a plurality of reference voltages to convert the $V_{OUT}(T_{int})$ into a digital signal represented by $D_{OUT}$. In the simplest case, quantizer 105 can be a one-bit clocked dynamic comparator in which $V_{OUT}$ is compared to a fixed DC voltage, $V_C$ at t=$T_{int}$. In the more involved case, quantizer 105 can be a multi-bit analog-to-digital converter (ADC).

Charge Injection Circuit 106 (FIG. 1)

Figure 3C:
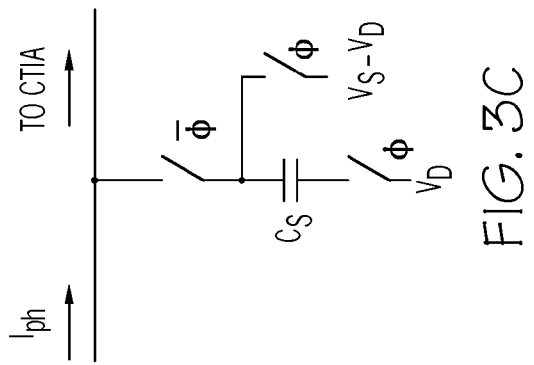
FIGS. 3A-3C illustrate examples of the charge injection circuit of the pixel in accordance with an embodiment of the present invention.
Figure 3B:
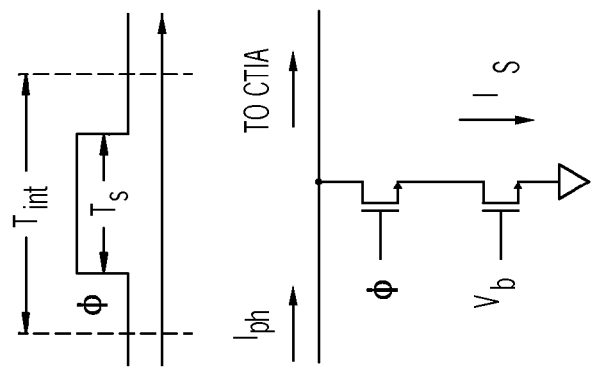
Figure 3A:
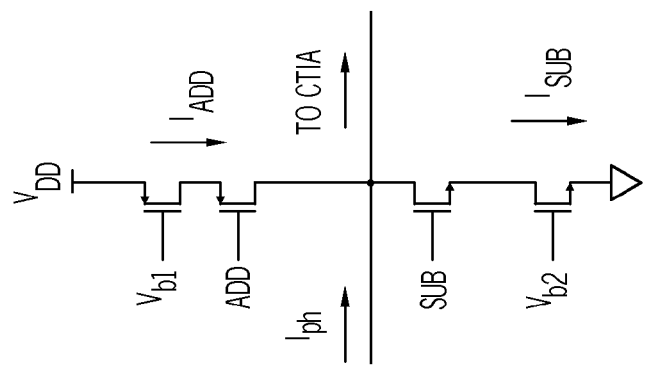

Referring to FIG. 1, charge injection circuit 106 performs the task of injecting a controlled current or net charge into the input node of CTIA 103 during the integration time. There are multiple IC techniques to implement this functionality. The following are example embodiments:

I. A controlled-amplitude and adjustable current, $I_{CAL}$, is directly added to or subtracted from the input of CTIA 103 (and subsequent integration onto $C_F$). In this case, if $I_{CAL}$ is remains unchanged during $T_{int}$, then the net added or subtracted charge during $T_{int}$, dented by $\Delta Q$, becomes equal to $I_{CAL} \times T_{int}$. FIG. 3A illustrates an example implementation of this where two current sources (top PMOS and bottom NMOS) can add $I_{CAL}=I_{ADD}$ or subtract $I_{CAL}=I_{SUB}$ by selecting ADD or SUB digital signals and applying them to the PMOS and NMOS transistors, respectively, in accordance with an embodiment of the present invention.

II. A fixed-amplitude current pulse, $I_S$, with a controllable width $T_S(T_S<T_{int})$, is used to subtract $\Delta Q=I_S \times T_S$ from the input of CTIA 103. FIG. 3B illustrates an example implementation of this where clock $\Phi$ connects $I_{CAL}$ onto the input of CTIA 103 for $T_S$ second during $T_{int}$ in accordance with an embodiment of the present invention.

III. A capacitor $C_{CAL}$ is first charged to an adjustable reference voltages, $V_{REF}$, and subsequently its stored charge $\Delta Q=C_{CAL} \times V_S$ is subtracted from the input of CTIA 103 (and hence $C_F$). FIG. 3C illustrates an example switch-level implementation of this where by toggling signal $\Phi$, $\Delta Q$ is subtracted from the input of CTIA 103 in accordance with an embodiment of the present invention. It is important to note that if the polarity of $V_S$ is reversed, a certain $\Delta Q$ can be added into the node as well.

Feedback Network 107 (FIG. 1)

Referring to FIG. 1, feedback network 107 effectively combines $D_{OUT}$ with charge injection circuit 106. The goal of this block is to determine and inject $\Delta Q$ within each measurement cycle based on $D_{OUT}$ of the previous cycles. An example of this feedback network is the case that when $D_{OUT}$ passes a certain threshold, a fixed charged is subtracted from the input. This process can also be more convoluted and the amount of charge added or subtracted can be a function of a plurality of $D_{OUT}$ values in the preceding cycles.

Background Subtraction

Referring to FIG. 1, $I_{ph}$ that is generated by photodiode 101 consists of two major parts. One part is the current which is a function of the analyte specific interactions with the recognition layer and the other is the "background" signal which is analyte-independent. Example background signals are the dark current leakage of photodiode 101 or the leakage of the excitation light into photodiode 101 in fluorescence-based biosensors. The background current is generally considered to be non-informative and it is preferred to be subtracted from the signal prior to detection. In the embodiments of the present invention, this current is subtracted by using charge injection circuitry 106 at every cycle.

Embodiment of the Pixel

Figure 4:
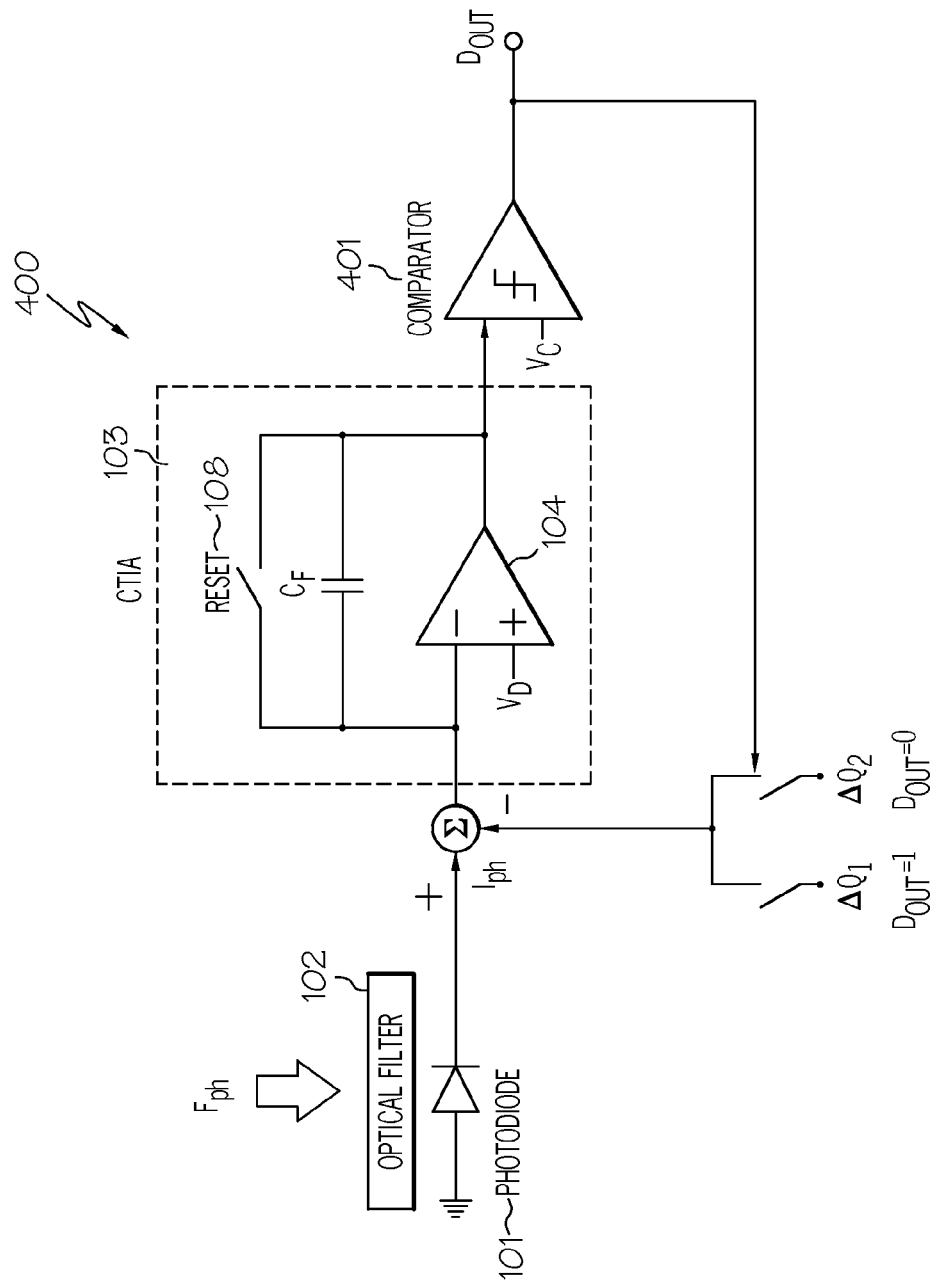
FIG. 4 illustrates an embodiment of the present invention of a biosensor pixel.

FIG. 4 illustrates an embodiment of a biosensor pixel 400 in accordance with an embodiment of the present invention. Referring to FIG. 4, in one embodiment of pixel 400, a sigma-delta ($\Sigma$-$\Delta$) modulator is implemented to measure $I_{ph}$. This circuit offers the advantage of noise shaping capabilities of $\Sigma$-$\Delta$ modulators, thereby improving the measurement dynamic range. In this pixel architecture, the feedback network effectively forms a Digital-to-Analog Converter (DAC) which subtracts $\Delta Q$ that represents $D_{OUT}$ in each cycle (i.e., ever $T_{int}$ seconds), while CTIA 103 acts as the integrator of the $\Sigma$-$\Delta$ modulator.

In an example embodiment, a 1-bit quantizer is used such that $D_{OUT}[n]=0$ for $V_{OUT}(nT_S)<V_C$, and $D_{OUT}[n]=1$ for $V_{OUT}(nT_S)>V_C$, where n is an integer number indicating the cycle number. The feedback network then subtracts $\Delta Q_1$ and $\Delta Q_2$ ($\Delta Q_1 > \Delta Q_2$) for $D_{OUT}[n]=1$ and $D_{OUT}[n]=0$, respectively at the next cycle, i.e., n+1, as shown in FIG. 4. The $D_{OUT}$ sequence can then be digitally filtered and down-sampled, for example using a decimation filter to estimate $I_{ph}$.

In one embodiment, $D_{OUT}$ changes $T_S$, the width of the current pulse $I_S$ ($T_S < T_{int}$) which is introduced at the input of CTIA 103. Hence, by making use of pulse-width-modulation (i.e., different pulse widths $T_s(1), T_s(2) \ldots T_s(N)$) for different quantized $D_{OUT}$ values $D_1, D_2 \ldots D_N$), it is possible to create the feedback DAC and enable the $\Sigma$-$\Delta$ operation.

In another embodiment, the capacitor $C_S$ is charged to different reference voltages $V_{REF}(1), V_{REF}(2), \ldots,$ and $V_{REF}(N)$, based on $D_{OUT}$ and its charge is then injected into the input of CTIA 103.

One advantage of the $\Sigma$-$\Delta$ modulator described herein is that it can also accommodate background subtraction without requiring any additional circuitry. This is extremely useful when the generated $I_{ph}$ contains a fix and un-informative component in the form of an offset. A widely known example is fluorescent-based biosensors with non-ideal optical filters, where the excitation light can reach the photodiode and create a large and relatively unchanging fixed background (offset) in $I_{ph}$. The approach to enable background subtraction enabled by the principles of the present invention is to subtract a fixed charge that represents the background signal during $T_{int}$ using the DAC and add the charge representing $D_{OUT}$ in addition to that.

Utilizing 1-bit quantizers offer lower complexity in $\Sigma$-$\Delta$ modulators, when compared to multi-bit quantizers. However, 1-bit $\Sigma$-$\Delta$ modulators inherently suffer from idle tones, when the input is a DC signal. It is widely known in the art that these idle tones occur due to the deterministic nature of the quantization noise and generally appear as tones with frequencies proportional to the input DC amplitude applied. In the present invention, such a problem is solved, for example, by using noise dithering which is known technique in the art. The idea is to add a white noise source 501 to the DC voltage source 502 at the input of comparator 401 (FIG. 4) as shown in FIG. 5 to randomize the quantization noise and remove the idle tones in accordance with an embodiment of the present invention.

Figure 5:
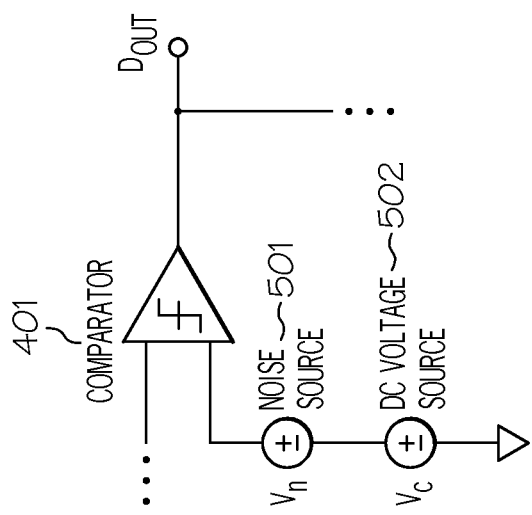
FIG. 5 illustrates removing the idle tones in accordance with an embodiment of the present invention.
Figure 5:
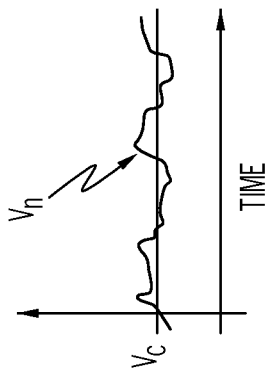

In summary, referring to FIGS. 4 and 5, one embodiment of the present invention for a pixel includes:

I. An integrated photodiode 101 connected to CTIA 103;

II. An optical filter 102;

III. A CTIA circuit 103 with its positive input connected to the controlled voltage source;

IV. A 1-bit comparator 401 with a noise dithered reference voltage 501; and V. A 1-bit DAC, which based on $D_{OUT}$, can inject different levels of charge into the input of CTIA 103 at each cycle.

Biosensor Array Architecture

Figure 6:
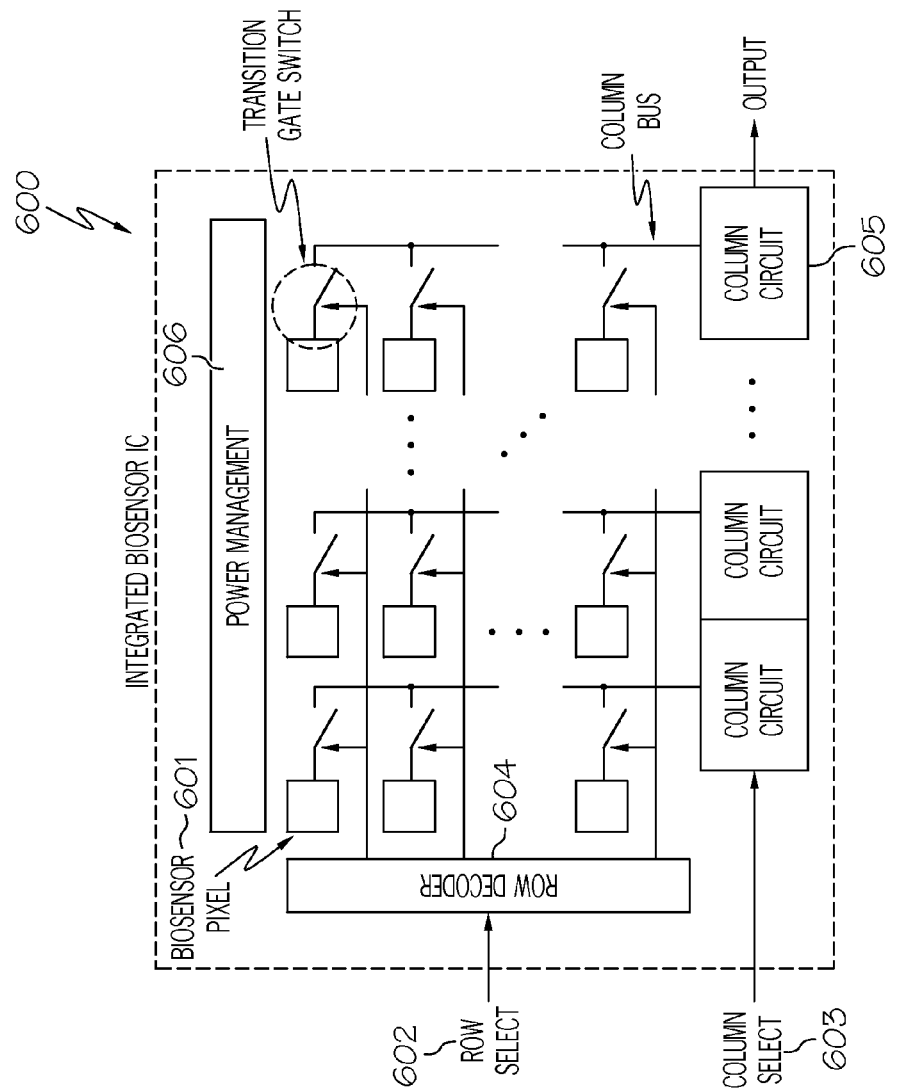
FIG. 6 illustrates an integrated biosensor array architecture in accordance with an embodiment of the present invention.

FIG. 6 illustrates an integrated optical biosensor array architecture 600 in accordance with an embodiment of the present invention. Pixels 601 are assembled in rows and columns within array 600. Individual pixels 601 are selected by using row and column deciders 602, 603, respectively. When a specific row within array 600 is selected by means of a row decoder 604, $D_{OUT}$ of all the pixels 601 in the selected row are connected to the shared column bus by means controlled by an electronic switch. This allows us to connect the outputs of the particular rows of interest to the column level circuitry 605.

The circuits within columns 605 can offer multiple functionalities. In one embodiment, it connects a selected output of a selected pixel 601 to the output of the IC using a column decoder. In other embodiments, it can perform additional tasks, such as digital filtering, digital decimation and storage.

Array 600 can also include an on-chip power management and voltage generation circuitry 606, which ensures that all the blocks receive the required supply and reference voltages. For example, power management circuit 606 is configured to ensure that each of the plurality of pixels 601 receive an appropriate supply and reference voltages. Array 600 can also include a clock and timing generation block to control the timing of the pulses which go through pixels 601.

Biosensing Setup:

Optical biosensor array 600 (FIG. 6) can be used in assays which take advantage of optical detection methods, such as using fluorescence or bioluminescence. In these systems, an optical signal generated by the chemistry involved in the biosensing process is created that indicates the presence and/or abundance of the analyte of interest. In the embodiments of the present invention, the biosensing process and the biological sample are placed on top and are optically interfaced and/or coupled to the optical filter which itself is placed on top of the integrated photodiodes and embedded sensing circuitry platform. This structure permits the development of a compact and integrated biosensor system, in which molecular recognition and sensing are done on the same platform.

Optical biosensor array 600 of the present invention can be used for almost any application where the parallel detection of optical signals in a biosensor is required. An example of such an application is affinity-based optical molecular detection, such as DNA and protein microarrays. In affinity-based biosensors, molecules that can specifically bind to the analyte molecules (generally referred to as the capturing probes) are immobilized on the surface on top of each pixel to form the recognition layer. The analyte molecules are typically labeled with reporters, such as fluorescent molecules or bioluminescence enzymes. Examples of such labels are molecules such as Cyanine dyes (e.g., Cy2, Cy3, Cy3.5, Cy5), FAM dyes, TARMA dyes, Texas Red®, luciferase and green fluorescence protein. The capturing events accumulate such labels in the intimate proximity of the surface on top of the pixel. Subsequently, by optically detecting captured probes using optical biosensor array 600, one can estimate the captured analyte and correlate its number to the concentration of the analyte in the sample.

Example Embodiment

An exemplary embodiment of a high-performance, parallel, and cost-efficient integrated optical biosensor array for bioluminescence-based DNA sequencing, generally referred to as pyrosequencing, is discussed below. This 12×12 biosensor array prototype is designed to demonstrate the advantage of the present invention in DNA sequencing applications. In particular, to demonstrate the degree by which the bulkiness and complexity of the instrumentation can be reduced while satisfying the stringent optical detection requirements of the pyrosequencing assay.

Figure 7A:
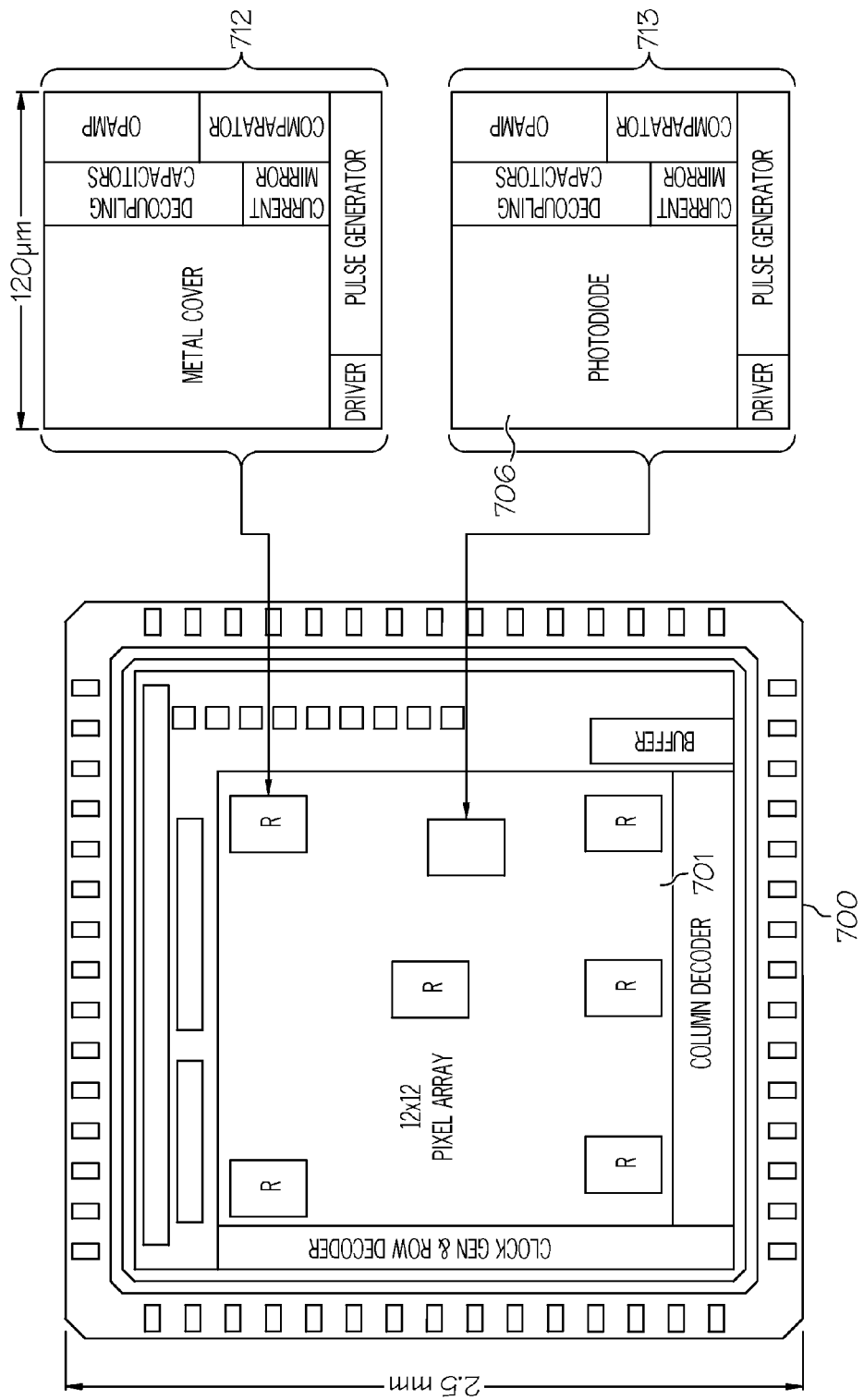
FIGS. 7A-7B illustrate the bioluminescence-based DNA sequencing system and the CMOS-integrated optical biosensor array in accordance with an embodiment of the present invention.
Figure 7B:
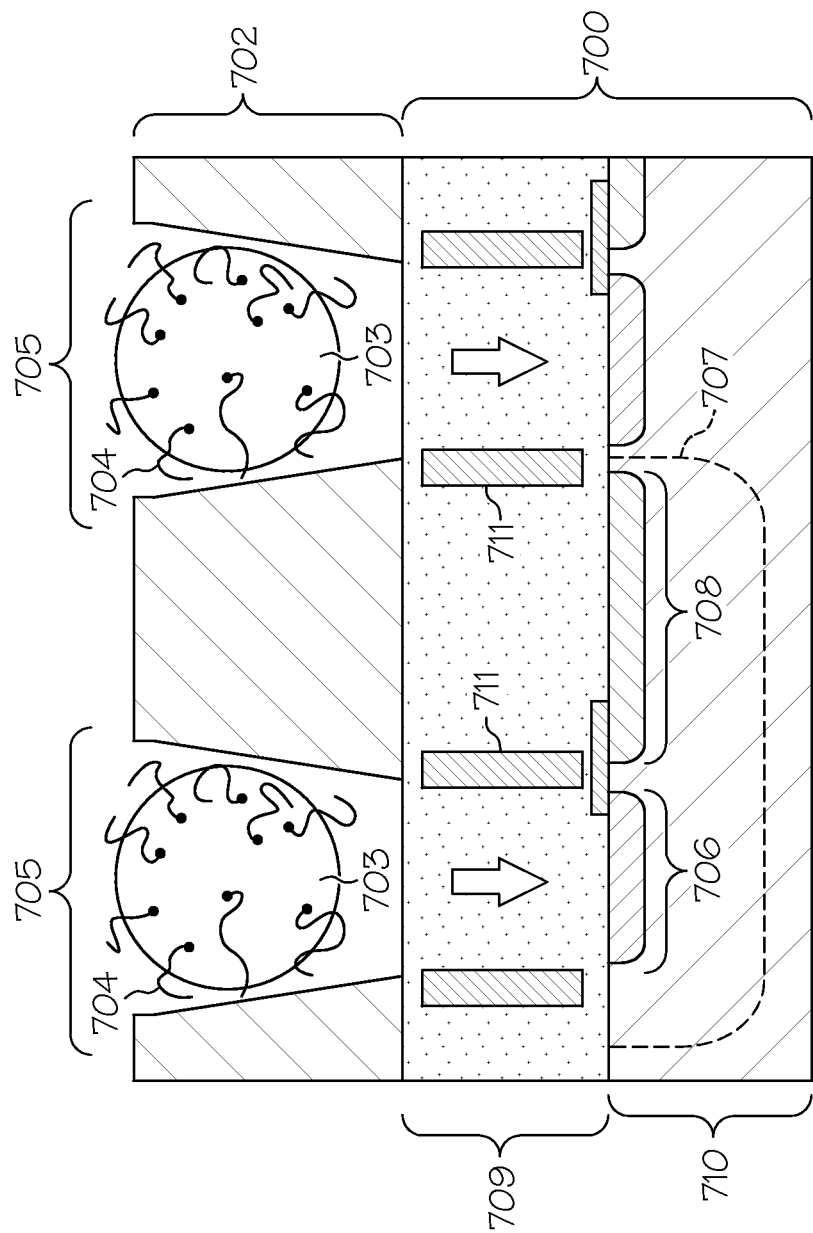

FIGS. 7A-7B illustrate the bioluminescence-based DNA sequencing system and the CMOS-integrated optical biosensor array in accordance with an embodiment of the present invention. Referring to FIG. 7A, FIG. 7A illustrates a top view micrograph of chip 700 that was fabricated using Taiwan Semiconductor Manufacturing Company (TSMC) 0.18 μm CMOS process. As illustrated in FIG. 7A, chip 700 includes 144 pixels where 6 pixels are used as calibration pixels 712, while the rest are used for detection 713. In the detection pixels 713, a photodiode 706 is integrated with a 1-bit Σ-Δ modulator according to the aforementioned embodiment of the present invention. Calibration pixel 712 is identical to detection pixel 713 except for the fact that photodiode 706 is fully covered with metal layers 709 as shown in FIG. 7B. The purpose of these pixels placed at different locations of chip 700 is to measure in real-time the temperature-dependent leakage (dark) current of the photodiodes and subtract their values from the $I_{ph}$ measured from the adjacent detection pixels 713 to arrive at a leakage of photodiodes 706.

The cross section of the biosensor array is illustrated in FIG. 7B. Pixel array 701 is aligned and placed underneath the micro-fabricated high-density picoliter micro-wells 705. Each micro-well 705 is placed exactly on top of the integrated photodiode 706 of each pixel 707 and a metal curtain 711 is built as the optical filter using metal layers 709 as of the process to ensure optical isolation between pixels. The walls of micro-wells 705 in this system are opaque and made of silicon. For biosensing, each micro-well 705 is loaded with micro-beads 703 which have DNA strands 704 covalently attached to them. This specific configuration is a widely known structure in DNA sequencing and is generally referred to as a bead-array 702.

Using pyrosequencing by applying the correct reactant, a sequence-dependent optical signal is generated in the individual wells 705 and subsequently is detected by the associated pixel. The wavelength of this signal is approximately 562 nm, making it compatible with CMOS-integrated on-chip photodiodes 706. The area of chip 700 is 2.5 mm×2.5 mm and consumes 50 mW of total power using 1.8V and 3V supplies for digital and analog blocks, respectively. Each pixel 707 size is 120 μm×120 μm and includes an N-well/P-sub photodiode 706 (~48% fill factor) and readout circuitry 708. Pixels 707 in silicon layer 710 of CMOS integrated chip 700 are separated from microwell bead array 702 via metal layers 709. Six metal-covered control pixels 707 are located at the periphery and the center of the array to measure and compensate for the temperature changes and dark current.

Figure 8A:
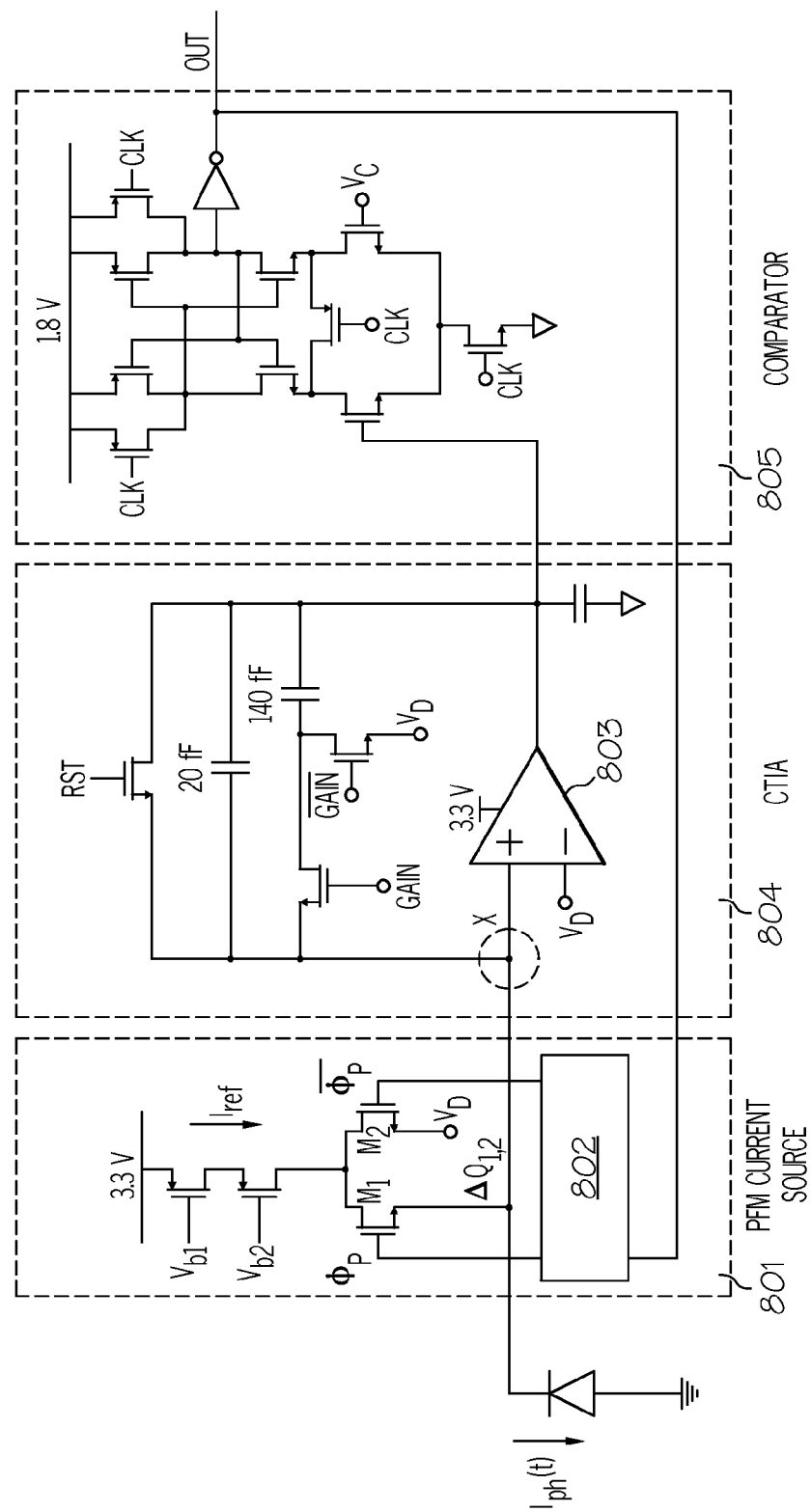
FIG. 8A is a transistor-level schematic of the pixel implementation in accordance with an embodiment of the present invention.
Figure 8B:
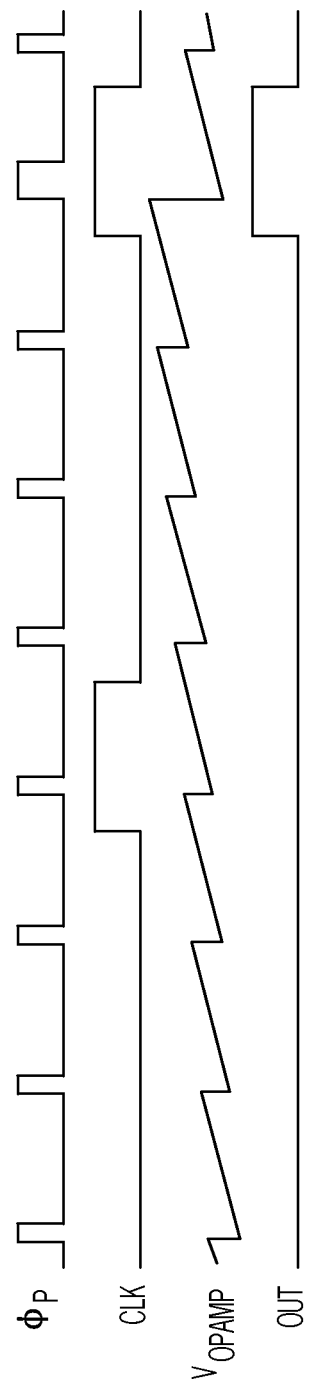
FIG. 8B is a timing diagram of the transistor-level schematic of the pixel implementation in accordance with an embodiment of the present invention.

FIG. 8A illustrates a transistor-level schematic of the pixel implementation in accordance with an embodiment of the present invention and FIG. 8B is a timing diagram of the transistor-level schematic of the pixel implementation in accordance with an embodiment of the present invention. Referring to FIGS. 8A and 8B, $I_{ph}(t)$ is generated by the photodiode biased at voltage $V_D$. Node X, the input of the CTIA, is where $\Delta Q_1$ and $\Delta Q_2$ required for the operation of the Σ-Δ modulator are injected. In the pyrosequencing method, the generated $I_{ph}(t)$ can vary within the fA to nA range and hence it is impractical to create $\Delta Q_1$ and $\Delta Q_2$ reliably using conventional CMOS current sources. Consequently, a programmable pulse frequency modulated (PFM) current source 801 is incorporated within each pixel. This circuit subtracts during each oversampling period the exact charge from node X that is necessary. This is achieved by current steering $I_{ref}$ into node X through M1 and M2 utilizing the Φp clock. The duration of Φp is programmable and controlled by a pulse generation circuitry 802 based on the value of ΔQ1 and ΔQ2. The net charge leaving node X is subsequently accumulated onto the feedback capacitor of in-pixel amplifier 803. Its value can be adjusted to 20 fF or 160 fF by setting the GAIN signal for high and low Σ-Δ loop-gain modes, respectively. The output of the CTIA 804 is then compared to the reference voltage, $V_C$, using a dynamic latch comparator 805 to generate the Σ-Δ output signal.

Figure 9:
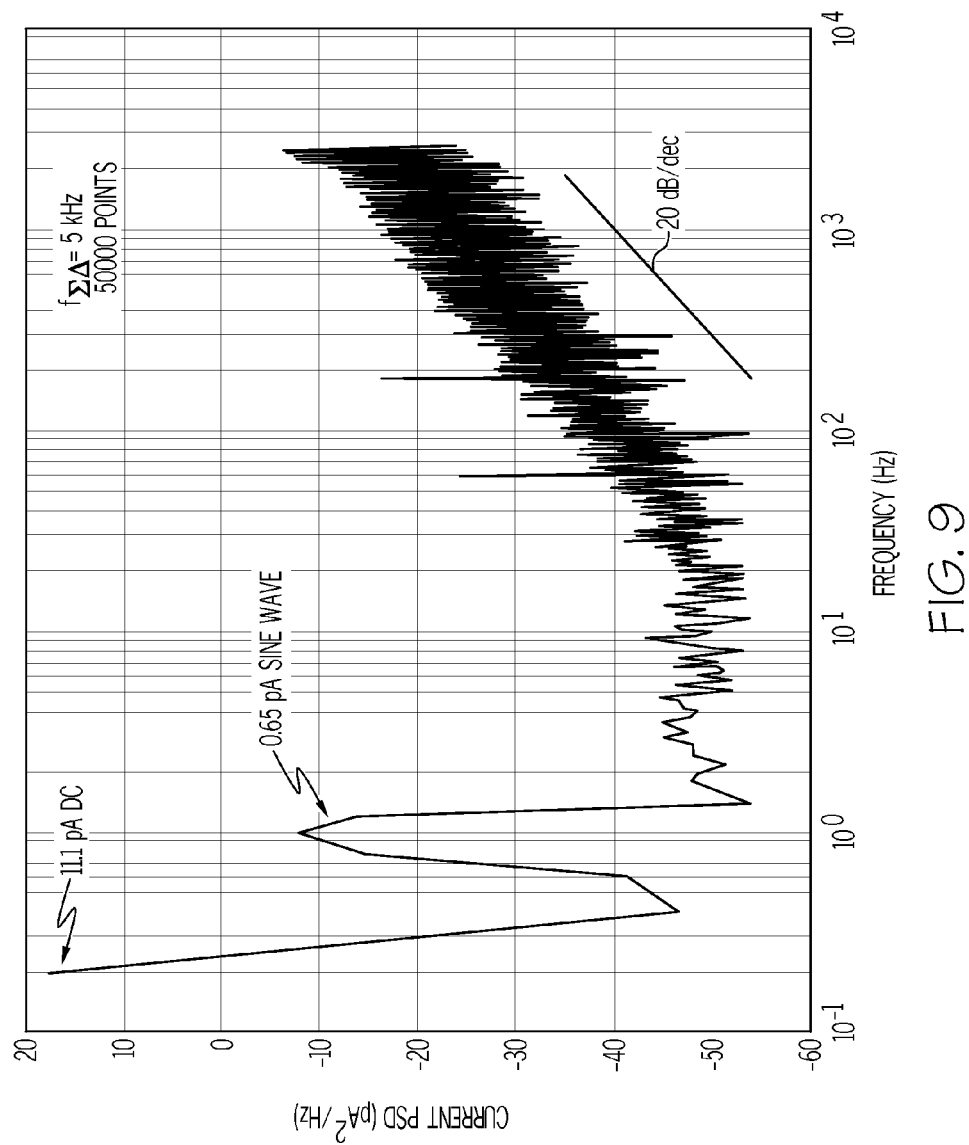
FIG. 9 illustrates the noise-shaped output of a single photodetector pixel in accordance with an embodiment of the present invention.

From the measured results, the in-pixel background subtraction circuitry is capable of generating $I_{CAL}$ in the 10 fA to 10 nA range, a 120 dB dynamic range. The noise floor (and therefore the Signal-to-Noise Ratio (SNR) in the system is determined by the shot-noise of $I_{ph}(t)$, and also the additional noise injected from PFM current source 801. However, minimum 40 dB Spurious-Free Dynamic Range (SFDR) is achievable within all the background level. FIG. 9 illustrates the noise-shaped output of a single photodetector pixel by depicting a graph of the frequency (Hz) versus current Power Spectral Density (PSD) (pA$^2$/Hz) in accordance with an embodiment of the present invention. In this particular experiment, a 1 Hz optical signal with DC background is applied by utilizing a blue Light-Emitting Diode (LED) device.

Figure 10:
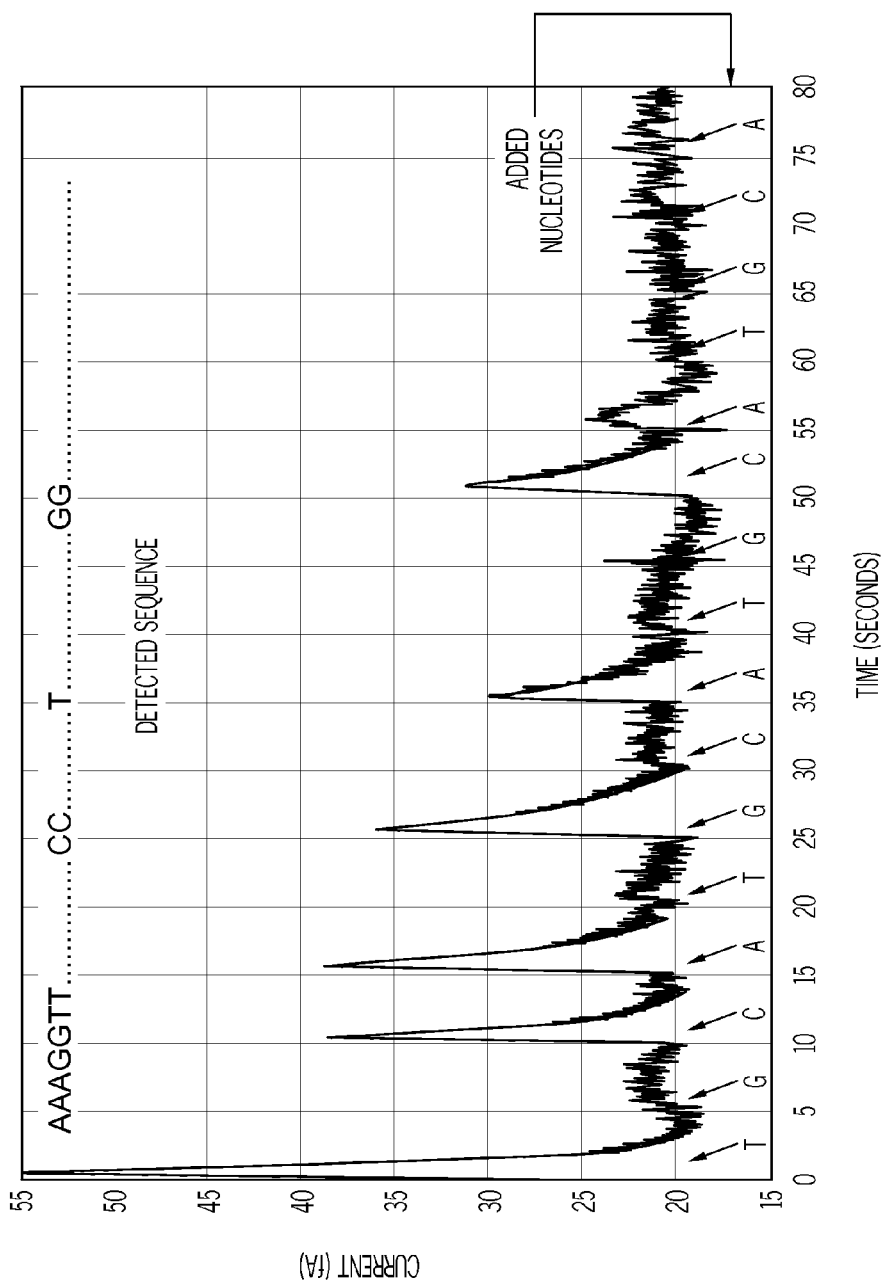
FIG. 10 illustrates the real-time measured photocurrent of one pixel during the sequence-by synthesis process in accordance with an embodiment of the present invention.

The performance of the chip discussed herein is also validated by performing pyrosequencing assay to detect the sequence of different DNA fragments. FIG. 10 illustrates the real-time measured photocurrent of one pixel during the sequence-by synthesis process by depicting a graph of the time (seconds) versus current (fA) in accordance with an embodiment of the present invention. The 320 fA background light of the assay was initially measured and was subtracted during the sequencing steps. The 40 pmol DNA sample along with the required reagents were placed in the reaction chamber. As illustrated, different nucleotides (T, G, C, and A) are sequentially added which are later decimated enzymatically. Only when a base-pair matching occurs (e.g., T is introduced to the A), the transient bioluminescence signal is produced which can be used to sequence the unknown DNA one step at a time. In this particular experiment, the recorded seven base DNA sequence (AAACCGGTTGCC) matched the control sequence that was placed in the sample as the "unknown DNA."

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The invention claimed is:

1. An optical biosensor pixel, comprising:
an integrated photodiode configured to convert an incident photon flux into a current;
an integrated optical filter coupled to said integrated photodiode, wherein said integrated optical filter is configured to select specific wavelengths and/or photon flux angles to reach said integrated photodiode from a biological sample;
a trans-impedance amplifier coupled to said integrated photodiode, wherein said trans-impedance amplifier is configured to convert said current into a voltage signal;
a quantizer circuit coupled to said trans-impedance amplifier, wherein said quantizer circuit is configured to convert a value of said voltage signal into a digital value;
a charge injection circuit coupled to said quantizer circuit, wherein said charge injection circuit is configured to place a fixed amount of net charge directly added to or subtracted from an input of said trans-impedance amplifier; and
a feedback network coupled to said quantizer circuit, wherein said feedback network comprises said charge injection circuit, wherein said feedback network is configured to control an operation of said charge injection circuit based on values of said digital value.

2. The optical biosensor pixel as recited in claim 1, wherein said trans-impedance amplifier comprises a capacitance trans-impedance amplifier circuit.

3. An optical biosensor pixel, comprising:
an integrated photodiode configured to convert an incident photon flux into a current;
an optical filter coupled to said integrated photodiode, wherein said optical filter is configured to select specific wavelengths and/or photon flux angles to reach said integrated photodiode from a biological sample;
a trans-impedance amplifier coupled to said integrated photodiode, wherein said trans-impedance amplifier is configured to convert said current into a voltage signal;
a controlled voltage source coupled to a positive input of said trans-impedance amplifier;
a 1-bit comparator coupled to said trans-impedance amplifier; and
a 1-bit digital-to-analog converter coupled to said 1-bit comparator, wherein said 1-bit digital-to-analog converter injects different levels of charge into an input of said trans-impedance amplifier at each cycle based on an output of said 1-bit comparator thereby subtracting a fixed charge at a next cycle from said current generated by said integrated photodiode.

4. The optical biosensor pixel as recited in claim 3, wherein said trans-impedance amplifier comprises a capacitance trans-impedance amplifier circuit.

5. The optical biosensor pixel as recited in claim 3, wherein a low-amplitude white noise source is inputted to said 1-bit comparator.

6. A biosensor array architecture, comprising:
a plurality of pixels assembled in rows and columns, wherein each of said plurality of pixels comprises:
an integrated photodiode configured to convert an incident photon flux into a current;
an optical filter coupled to said integrated photodiode, wherein said optical filter is configured to select specific wavelengths and/or photon flux angles to reach said integrated photodiode from a biological sample;
a trans-impedance amplifier coupled to said integrated photodiode, wherein said trans-impedance amplifier is configured to convert said current into a voltage signal;
a controlled voltage source coupled to a positive input of said trans-impedance amplifier;
a 1-bit comparator coupled to said trans-impedance amplifier; and
a 1-bit digital-to-analog converter coupled to said 1-bit comparator, wherein said 1-bit digital-to-analog converter injects different levels of charge into an input of said trans-impedance amplifier at each cycle based on an output of said 1-bit comparator thereby subtracting a fixed charge at a next cycle from said current generated by said integrated photodiode; and
row and column deciders coupled to said plurality of pixels, wherein said row and column deciders are configured to select individual pixels of said plurality of pixels.

7. The biosensor array architecture as recited in claim 6 further comprises:
   a row decoder coupled to said plurality of pixels, wherein said row decoder is configured to select a specific row within said biosensor array architecture.

8. The biosensor array architecture as recited in claim 6 further comprises:
   a power management circuit configured to ensure that each of said plurality of pixels receive an appropriate supply and reference voltage.

* * * * *